(12) United States Patent
Hakozaki

(10) Patent No.: US 9,676,696 B2
(45) Date of Patent: *Jun. 13, 2017

(54) REGULATION OF MAMMALIAN KERATINOUS TISSUE USING SKIN AND/OR HAIR CARE ACTIVES

(75) Inventor: Tomohiro Hakozaki, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 590 days.

This patent is subject to a terminal disclaimer.

(21) Appl. No.: 12/692,826

(22) Filed: Jan. 25, 2010

(65) Prior Publication Data

US 2010/0189669 A1     Jul. 29, 2010

Related U.S. Application Data

(60) Provisional application No. 61/148,081, filed on Jan. 29, 2009.

(51) Int. Cl.
| | | |
|---|---|---|
| *A61K 31/7016* | (2006.01) | |
| *A61K 31/7024* | (2006.01) | |
| *A61K 31/047* | (2006.01) | |
| *A61K 31/166* | (2006.01) | |
| *C07C 51/41* | (2006.01) | |
| *C07C 59/72* | (2006.01) | |

(52) U.S. Cl.
CPC ............ *C07C 51/41* (2013.01); *C07C 51/412* (2013.01); *C07C 59/72* (2013.01)

(58) Field of Classification Search
None
See application file for complete search history.

(56) References Cited

U.S. PATENT DOCUMENTS

| | | |
|---|---|---|
| 3,755,560 A | 8/1973 | Bolens |
| 3,775,560 A | 11/1973 | Ebeling et al. |
| 4,421,769 A | 12/1983 | Dixon et al. |
| 4,560,553 A * | 12/1985 | Zupan .................. 514/20.5 |
| 4,835,148 A | 5/1989 | Barford et al. |
| 5,425,948 A | 6/1995 | Olivieri |
| 5,612,038 A | 3/1997 | Gedouin et al. |
| 5,723,482 A | 3/1998 | Degwert |
| 5,730,972 A | 3/1998 | Simon |
| 5,821,250 A | 10/1998 | Wu et al. |
| 5,824,326 A * | 10/1998 | Crotty et al. .................. 424/401 |
| 5,882,658 A | 3/1999 | Simon |
| 5,918,590 A | 7/1999 | Burkett et al. |
| 5,972,957 A | 10/1999 | Wu et al. |
| 5,981,547 A | 11/1999 | Wu et al. |
| 6,013,270 A | 1/2000 | Hargraves |
| 6,060,547 A | 5/2000 | Canter et al. |
| 6,153,208 A | 11/2000 | McAtee |
| 6,190,678 B1 | 2/2001 | Hasenoehrl |
| 6,221,372 B1 | 4/2001 | Golz Berner |
| 6,238,678 B1 * | 5/2001 | Oblong et al. .................. 424/401 |
| 6,267,971 B1 | 7/2001 | Breton |
| 6,281,203 B1 | 8/2001 | Touzan |
| 6,338,855 B1 | 1/2002 | Albacarys |
| 6,825,161 B2 | 11/2004 | Shefer |
| 6,831,107 B2 | 12/2004 | Dederen |
| 6,846,812 B2 | 1/2005 | Dalko |
| 6,872,401 B2 | 3/2005 | Seyler |
| 6,964,954 B2 | 11/2005 | Dalko |
| 6,998,129 B2 | 2/2006 | Breton |
| 7,208,460 B2 | 4/2007 | Shefer |
| 7,300,649 B2 | 11/2007 | Tanojo et al. |
| 7,916,910 B2 | 3/2011 | Cotton |
| 7,970,456 B2 | 6/2011 | Preece |
| 7,999,008 B2 | 8/2011 | Bernard |
| 8,287,846 B2 | 10/2012 | Rampoldi |
| 8,486,376 B2 | 7/2013 | Friedman |
| 2002/0058010 A1 | 5/2002 | Picard Lesboueyries |
| 2003/0091665 A1 | 5/2003 | Lu |
| 2003/0165547 A1 | 9/2003 | Picard |
| 2003/0224028 A1 | 12/2003 | Galey |
| 2003/0232091 A1 | 12/2003 | Shefer |
| 2004/0175347 A1 | 9/2004 | Bissett |

(Continued)

FOREIGN PATENT DOCUMENTS

| | | |
|---|---|---|
| DE | 10223233 A1 | 12/2003 |
| DE | 102005061520 A1 | 7/2007 |

(Continued)

OTHER PUBLICATIONS

U.S. Appl. No. 12/841,980, filed Jul. 2010, Hakozaki et al.*
U.S. Appl. No. 13/298,985, filed Nov. 2011, Hakozaki et al.*
Bullerman, et al. "Inhibition of growth and aflatoxin production by cinnamon and clove oils. Cinnamic aldehyde and eugenol" Journal of Food Science (1977), vol. 42, Issue 4, pp. 1107-1109.*
Csóka, G., et al. "Application of sucrose fatty acid esters in transdermal therapeutic systems." European journal of pharmaceutics and biopharmaceutics 65.2 (2007): 233-237.*
U.S. Appl. No. 13/189,000, filed Jul. 22, 2011, Cheri Lynn Swanson.
U.S. Appl. No. 13/189,089, filed Jul. 22, 2011, Cheri Lynn Swanson.
U.S. Appl. No. 13/189,138, filed Jul. 22, 2011, Cheri Lynn Swanson.
U.S. Appl. No. 13/189,182, filed Jul. 22, 2011, Cheri Lynn Swanson.

(Continued)

*Primary Examiner* — Sue Liu
*Assistant Examiner* — Daniel Branson
(74) *Attorney, Agent, or Firm* — Carl J. Roof

(57) ABSTRACT

Personal care compositions containing an active selected from the group consisting of phlorogine, phlorgine BG, deoxyArbutin, sucrose dilaurate, bakuchiol, pyrenoine, millet, arlatone dioic acid, cinnamic acid, ferulic acid, achromaxyl, methyl nicotinamide, oil soluble licorice extract, folic acid, undecylenic acid, zinc undecylenate, L-tryptophan, thiamine HCl, hexylresorcinol, lipidami red vine, dragosine, methyl gentisate, inositol, symdiol 68, laminaine, their salts, their derivatives, their precursors, and/or combinations thereof. Methods for regulating the condition of mammalian keratinous tissue by topically applying the personal care compositions are also provided.

20 Claims, No Drawings

(56) References Cited

U.S. PATENT DOCUMENTS

| | | |
|---|---|---|
| 2005/0019356 A1 | 1/2005 | Bissett et al. |
| 2005/0025737 A1 | 2/2005 | Sebagh |
| 2005/0069566 A1 | 3/2005 | Tamarkin |
| 2005/0075407 A1 | 4/2005 | Tamarkin |
| 2005/0118218 A1 | 6/2005 | Cassin |
| 2005/0147631 A1 | 7/2005 | Goldstein |
| 2005/0164991 A1 | 7/2005 | Dalko |
| 2005/0220726 A1 | 10/2005 | Pauly |
| 2005/0249763 A1 | 11/2005 | Legendre |
| 2005/0255060 A1* | 11/2005 | Oblong et al. ............ 424/59 |
| 2005/0271692 A1 | 12/2005 | Gervasio-Nugent |
| 2006/0008428 A1 | 1/2006 | Seyler |
| 2006/0039938 A1 | 2/2006 | Josse |
| 2006/0057092 A1 | 3/2006 | Marion |
| 2006/0141078 A1 | 6/2006 | Guillou |
| 2006/0198800 A1 | 9/2006 | Dilallo |
| 2006/0263438 A1 | 11/2006 | Biatry |
| 2006/0272103 A1 | 12/2006 | Barbarat |
| 2006/0275237 A1 | 12/2006 | Bissett |
| 2006/0293207 A1 | 12/2006 | Porter |
| 2007/0059269 A1 | 3/2007 | Bernard |
| 2007/0154425 A1 | 7/2007 | Potin |
| 2007/0248633 A1 | 10/2007 | Baldo |
| 2007/0297999 A1 | 12/2007 | Fonolla |
| 2008/0008673 A1 | 1/2008 | Willemin |
| 2008/0014162 A1 | 1/2008 | Willemin |
| 2008/0069784 A1* | 3/2008 | Millikin et al. ............ 424/59 |
| 2008/0081055 A1 | 4/2008 | Cassin |
| 2008/0107679 A1 | 5/2008 | Dilallo |
| 2008/0119527 A1 | 5/2008 | Baldo |
| 2008/0159970 A1 | 7/2008 | Willemin |
| 2008/0183250 A1 | 7/2008 | Tanojo |
| 2008/0200545 A1 | 8/2008 | Aubrun-Sonneville |
| 2008/0226756 A1 | 9/2008 | Willemin |
| 2009/0016971 A1 | 1/2009 | Gaudry |
| 2009/0016974 A1 | 1/2009 | Pruche |
| 2009/0018200 A1 | 1/2009 | Willemin |
| 2009/0022819 A1 | 1/2009 | Gueniche |
| 2009/0035241 A1 | 2/2009 | Cassin |
| 2009/0041691 A1 | 2/2009 | Candau |
| 2009/0110651 A1 | 4/2009 | Moussou |
| 2009/0285868 A1 | 11/2009 | Richard |
| 2009/0324663 A1 | 12/2009 | Legendre |
| 2010/0003236 A1 | 1/2010 | Dalko |
| 2010/0086502 A1 | 4/2010 | Lucet-Levannier |
| 2010/0112100 A1 | 5/2010 | Willemin |
| 2010/0150853 A1 | 6/2010 | Cassin |
| 2010/0183528 A1 | 7/2010 | Maloney |
| 2011/0097286 A1 | 4/2011 | Swanson |

FOREIGN PATENT DOCUMENTS

| | | |
|---|---|---|
| EP | 1074262 B1 | 4/2005 |
| EP | 1607083 A1 * | 12/2005 |
| EP | 1759688 A1 | 3/2007 |
| EP | 1997537 A2 | 12/2008 |
| FR | 2655268 A1 | 6/1991 |
| FR | 2803200 A1 | 7/2001 |
| FR | 2803201 A1 | 7/2001 |
| FR | 2838340 A1 | 10/2003 |
| JP | 63057510 A | 3/1988 |
| JP | 05043446 | 2/1993 |
| JP | 05186324 | 7/1993 |
| JP | 10158148 | 6/1998 |
| JP | 2001270815 | 10/2001 |
| JP | 2002179547 | 6/2002 |
| JP | 2003226637 | 8/2003 |
| JP | 2004331592 | 11/2004 |
| JP | 2005206573 | 8/2005 |
| JP | 2005213171 | 8/2005 |
| JP | 2005304363 | 11/2005 |
| JP | 2006045140 | 2/2006 |
| JP | 2006290766 | 10/2006 |
| JP | 2007153752 | 6/2007 |
| JP | CA 2641106 A1 * | 8/2007 ............ A61K 8/4986 |
| JP | 2008237057 | 10/2008 |
| WO | WO 9617588 A1 | 6/1996 |
| WO | WO9822085 A1 | 5/1998 |
| WO | WO 9826755 A1 | 6/1998 |
| WO | WO 9913861 A1 | 3/1999 |
| WO | WO 9955303 A1 | 11/1999 |
| WO | WO 0101816 A1 | 1/2001 |
| WO | WO 0101933 A2 | 1/2001 |
| WO | WO 0101950 A1 | 1/2001 |
| WO | WO 0101951 A1 | 1/2001 |
| WO | WO 0101952 A1 | 1/2001 |
| WO | WO 0102028 A2 | 1/2001 |
| WO | WO 0102477 A1 | 1/2001 |
| WO | WO 0102478 A1 | 1/2001 |
| WO | WO 0102479 A1 | 1/2001 |
| WO | WO 2004004673 A1 | 1/2004 |
| WO | WO200620164 A1 | 2/2006 |
| WO | WO 2007106501 A2 * | 9/2007 |
| WO | WO 2009008397 A1 * | 1/2009 |
| WO | WO 2009/047443 A2 | 4/2009 |
| WO | WO 2010088225 A2 | 8/2010 |

OTHER PUBLICATIONS

American Beauty Cosmetics, Extra Clean Balancing Tonic, Date Published Sep. 2004, www.gnpd.com 2 pages.

American Beauty Cosmetics, Fabulous Forth Gel Cleanser, Date Published Sep. 2004, www.gnpd.com 2 pages.

Aramis Lab Series for Men, Trifecta Triple Effect Formula Skincare Spray, Date Published Feb. 2002, www.gnpd.com, 2 pages.

Avon Colour Cosmetics, Hide and Clear Kit Acne Treatment, Date Published Jul. 2006, www.gnpd.com, 2 pages.

Avon Mark Spots Away, AM-PM Blemish Neutralizer, Date Published Nov. 2003, www.gnpd.com, 2 pages.

Avon, Clear Finish Great Complexion, Concealer with Acne Treatment, Date Published Jan. 2002, www.gnpd.com, 2 pages.

Avon, Clear Finish Oil-Free Foundation, Date Published Aug. 1997, www.gnpd.com, 2 pages.

Avon, Dab Action Face Clearing Foundation, Date Published Sep. 2005, www.gnpd.com, 2 pages.

Avon, Finish Great Complexion, Pressed Powder, Date Published Jan. 2002, www.gnpd.com, 2 pages.

Avon, Project Amber, Personal Match Foundation, Date Published Jan. 2005, www.gnpd.com, 2 pages.

Biotherm Biopur Pore Reducer, Smoothing Perfector Serum, Date Published Feb. 2006, www.gnpd.com, 2 pages.

Bissett, Donald L., et al.: "Reduction in the appearance of facial hyperpigmentation by topical N-undecyl-10-enoyl-L-phenylalanine and its combination with niacinamide." Dec. 2009 (Dec. 2009), *Jo8urnal of Cosmetic Dermatology*, Dec. 1009 LNKD-PUBMED: 19958429, vol. 8, NR. 4 pp. 260-266, XP9144669, ISSN: 1473-2165.

Bliss Products Instant Mattification, 10-Minute Deep Cleaning Treatment, Date Published Apr. 2005, www.gnpd.com, 2 pages.

Bliss, Steep Clean Skincare, Mattifying Moisturizer, Date Published Jan. 2009, www.gnpd.com, 2 pages.

Bobbi Brown, Oil Control Lotion SPF 15, Date Published Jun. 2008, www.gnpd.com, 2 pages.

Bobbi Brown, Purifying Gel Cleanser, Date Published Jul. 2002, www.gnpd.com, 2 pages.

Bobbi Brown, Shine Control Face Gel, Date Published Jul. 2002, www.gnpd.com, 2 pages.

Bobbi Brown, Skin Care to Go Kit, Date Published Oct. 2002, www.gnpd.com, 2 pages.

Boots Retail, Boots Face Botanics, Balancing Shine Control Treatment, Date Published Oct. 2004, www.gnpd.com, 2 pages.

Boots Retail, Pore Perfecting Light Night Cream, Date Published Oct. 2004, www.gnpd.com, 2 pages.

Clinique Colour Cosmetics; Superfit Makeup, Date Published Nov. 2009, www.gnpd.com, 4 pages.

Clinique Skin Care; 3-Step Skin Care System, Date Published Jun. 2009, www.gnpd.com, 5 pages.

Clinique Acne Solutions Quick Clearing Pads, Date Published Jun. 2003, www.gnpd.com. 2 pages.

(56) References Cited

OTHER PUBLICATIONS

Clinique Acne Solutions; Body Spray Repackaging, Date Published Oct. 2007, www.gnpd.com, 2 pages.
Clinique Acne Solutions; Clarifying Lotion, Date Published Oct. 2007, www.gnpd.com, 2 pages.
Clinique Acne Solutions; Cleansing Foam, Date Published Oct. 2007, www.gnpd.com, 2 pages.
Clinique Acne Solutions; Clearing Moisturizer, Date Published Aug. 2007, www.gnpd.com, 2 pages.
Clinique Acne Solutions; Colour Cosmetics, Clearing Concealer, Date Published Jul. 2009, www.gnpd.com, 3 pages.
Clinique Acne Solutions; Colour Cosmetics, Liquid Make-up; Date Published Apr. 2010, www.gnpd.com, 3 pages.
Clinique Acne Solutions; Oil-Control Cleansing Mask, Date Published Jul. 2009, www.gnpd.com, 3 pages.
Clinique Active White, Daily Moisture, Date Published Jan. 2006, www.gnpd.com, 2 pages.
Clinique Clarifying Makeup, Date Published May 2000, www.gnpd.com, 1 page.
Clinique Skin Supplies for Men; Oil Control Hydrator, Date Published Aug. 2007, www.gnpd.com, 2 pages.
Clinique Skincare, Dramatically Different Moisturizing Gel Repackaging, Date Published Feb. 2006, www.gnpd.com, 2 pages.
Clinique Skincare, Turnaround 15-Minute Facial, Date Published Jan. 2006, www.gnpd.com, 2 pages.
Clinique Skincare, Turnaround Concentrate, Date Published Jan. 2006, www.gnpd.com, 2 pages.
Clinique Superfit Makeup, Data Published May 1999, www.gnpd.com, 2 pages.
Clinique, Dramatically Different Moisturizing Gel, Date Published Jul. 2004, www.gnpd.com, 2 pages.
Clinique, Superdefense, Triple Action Moisturizer, Date Published Sep. 2004, www.gnpd.com, 2 pages.
*CTFA Cosmetic Ingredient Handbook*, Second Edition (1992).
Database GNPD (Online) Mintel; Apr. 2001 (Apr. 2001), "Idealist Skin Refinisher," Skin Refinisher, XP002608983, Database accession No. 93035 the whole document.
Database GNPD (Online) Mintel; Apr. 2008 (Apr. 2008), "Extra Concentrated Brightening Essence," XP002610255, Database accession No. 887317 the whole document.
Database GNPD (Online) Mintel; Apr. 2010 (Oct. 2001), "Toner," XP002610262, Database accession No. 1309852 the whole document.
Database GNPD (Online) Mintel; Aug. 2004 (Aug. 2004), "Clear White Peel-Off T-Zone Mask," XP002610261, Database accession No. 291044 the whole document.
Database GNPD (Online) Mintel; Aug. 2004 (Aug. 2004), "SK-II Facial Whitening Mask," XP002610265, Database accession No. 290213 the whole document.
Database GNPD (Online) Mintel; Aug. 2005 (Aug. 2008), "Pore Minimizing Matifying Milk," XP002610260, Database accession No. 384090 the whole document.
Database GNPD (Online) Mintel; Aug. 2006 (Aug. 2006), "Moisture Milk Combination Oily to Oily Skin," XP002610257, Database accession No. 573002 the whole document.
Database GNPD (Online) Mintel; Jul. 2008 (Jul. 2008), "Extra Brightening Moisture Lotion," XP002610254, Database accession No. 940552 the whole document.
Database GNPD (Online) Mintel; Jul. 2008 (Jul. 2008), "Skin Shine Control Facial Foam," XP002610258, Database accession No. 556086 the whole document.
Database GNPD (Online) Mintel; Jul. 2009 (Jul. 2009), "Brightening Moisture Gel Cream," XP002610256, Database accession No. 1133334 the whole document.
Database GNPD (Online) Mintel; Jun. 2009 (Jun. 2009) "Anti-Ageing Night Cream," Database accession No. 1122741 the whole document.
Database GNPD (Online) Mintel; Jun. 2010 (Jun. 2010), "Skin Lightening Body Milk," XP002610264, Database accession No. 1348299 the whole document.
Database GNPD (Online) Mintel; Mar. 2010 (Mar. 2010), "Lotion," XP002610263, Database accession No. 1296673 the whole document.
Database GNPD (Online) Mintel; Sep. 2007 (Sep. 2007), "Bionic Serum 10," XP002610259, Database accession No. 738557 the whole document.
Database GNPD 9 (Online) Mintel: Nov. 2004 (Nov. 2004), "Pure Zone Purifying Clarifying Toner Step 2," XP002608984, Database accession No. 316473 the whole document.
Del Laboratories Sally Hansen Beyond Perfect European Pedicure, 18 Hour Dry Skin Foot Crème, Date Published May 2005, www.gnpd.com, 2 pages.
Del Laboratories Sally Hansen Beyond Perfect European Pedicure, Extra Strength Callus Remover Gel, Date Published May 2005, www.gnpd.com, 2 pages.
Del Laboratories Sally Hansen Beyond Perfect European Pedicure, Foot Scrub Date Published Feb. 2005, www.gnpd.com, 2 pages.
Del Laboratories Sally Hansen Beyond Perfect European Pedicure, Luxurious Leg & Foot Mask, Date Published May 2005, www.gnpd.com, 2 pages.
Estee Lauder Good Skin, Acne Care, Date Published Dec. 2004, www.gnpd.com, 2 pages.
Estee Lauder Idealist Skin Refresher, Date Published Dec. 2006, www.gnpd.com, 2 pages.
Estee Lauder Oil Control, Anti-Acne Gel, Date Published Dec. 2006, www.gnpd.com, 1 page.
Estee Lauder Oil Control, Male Skincare Range, Date Published Dec. 2006, www.gnpd.com, 1 page.
Good Skin Dermcare, Good Skin, Makeup, Date Published Dec. 2005, www.gnpd.com, 2 pages.
Good Skin Dermcare, Good Skin, Mattifying Gel, Date Published Oct. 2005, www.gnpd.com, 2 pages.
Good Skin Dermcare, Good Skin, Medicated Cleanser, Date Published Oct. 2005, www.gnpd.com, 2 pages.
Graham Webb Bibo Healthy Skincare, Girl's Best Friend Age-Defying Complex, Date Published Mar. 2002, www.gnpd.com, 2 pages.
Grassroots Life, Face Cleanser, Date Published Oct. 2005, www.gnpd.com, 2 pages.
Grassroots Life, Without a Trace Face Cleanser, Date Published Jan. 2006, www.gnpd.com, 2 pages.
H2O Plus, Facial Care Range, Date Published Aug. 2007, www.gnpd.com, 2 pages.
High-Tech Bioactive Substances Catalogue, Biotech Marin, www.biotechmarine.com; France 16 pages.
International Search Report, dated Dec. 8, 2010, PCT/US2010/22153.
International Search Report, dated Mar. 16, 2011, PCT/US2010/022153.
International Search Report, PCT/US2010/042845, Jul. 22, 2010; 128 pages; WO/ISA p. 6.
International Search Report, PCT/US2010/042846, Jul. 22, 2010; 117 pages; WO/ISA p. 6.
International Search Report, PCT/US2010/042857, Jul. 22, 2010; 175 pages.
International Search Report, PCT/US2010/042860, Jul. 22, 2010, 138 pages.
International Search Report, PCT/US2010/042861, Jul. 22, 2010, 51 pages.
Jafra Balance Dynamics, Balancing Lotion SPF 15, Date Published Jan. 2008; www.gnpd.com, 2 pages.
Jafra Cosmetics, Balance/Control Dynamics, Balance Control Mask, Date Published Jun. 2010, www.gnpd.com; 2 pages.
Kiehl's Blue Herbal Gel Cleanser, Date Published Jun. 2004, www.gnpd.com, 1 page.
Kiehl's Blue Herbal Moisturizer, Date Published Jun. 2004, www.gnpd.com, 2 pages.
Kiehl's Blue Herbal Spot Treatment, Date Published Jun. 2004, www.gnpd.com, 2 pages.
Laminaria Saccharina Extract: CTFA ID 7647; International Cosmetic Ingredient Dictionary and Handbook, $11^{th}$ Edition, Printed Edition Page No. 1204; 2 pages.

(56) References Cited

OTHER PUBLICATIONS

L'Oreal Demo-Expertise Acne Response, Intensive Adult Acne Peel, Feb. 2006, www.gnpd.com, Date Published Feb. 2006, 3 pages.
L'Oreal Demo-Expertise Pure Zone, Skin Clarifying Cleansing Cloths, Date Published Apr. 2003, www.gnpd.com, 3 pages.
L'Oreal Demo-Expertise Pure Zone, Step 1 Pore Unclogging Scrub Cleanser, Date Published May 2004, www.gnpd.com, 2 pages.
L'Oreal Pure Zone Continuous Action Spot Check, Salicylic Acid Breakout Treatment, Date Published Aug. 2002, www.gnpd.com, 2 pages.
L'Oreal Pure Zone Continuous Action, Step 1 Skin Balancing Cream Cleanser, Date Published May 2002, www.gnpd.com, 2 pages.
L'Oreal Pure Zone Continuous Action, Step 2 Pore Tightening Astringent, Date Published May 2002, www.gnpd.com, 2 pages.
L'Oreal Pure Zone Continuous Action, Step 3 Skin Relief Oil-Free Moisturizer, Date Published May 2002, www.gnpd.com, 2 pages.
Lab Series Research Centre , Triple Benefit Post-Shave Remedy, Date Published Sep. 2006, www.gnpd.com, 1 page.
Lab Series Research Centre, Lab Series Skincare, Anti-Acne Gel, Date Published Mar. 2007, www.gnpd.com 2 pages.
Lab Series Research Centre, Lab Series Skincare, Oil Control Face Wash, Date Published Mar. 2007, www.gnpd.com 2 pages.
Lab Series Research Centre, Lab Series Skincare, Oil Control Towelettes, Date Published Mar. 2007, www.gnpd.com 2 pages.
MacDonald, Veronica; Spa Treatments, "Spa Products Are Now a Tangible Take-Home Concept as More America Relieved Stress Get Well and Indulge in New Found Luxuries"; Happi Household and Personal Products Industry; 5 pages.
Merle Norman Cosmetic Studios, Clear Complexion Spot Treatment, Date Published Jan. 2008, www.gnpd.com, 2 pages.
Neutrogena MoistureShine, Lip Smoother, Date Published Dec. 2008, www.gnpd.com, 2 pages.

Oikarinen, "The Aging of Skin: Chronoaging Versus Photoaging," *Photodermatol. Photoimmunol. Photomed.*, vol. 7, pp. 3-4, 1990.
Orangehrzn: "Oil Control with Phlorogine—Smart Skin Care," Apr. 28, 2005 (Apr. 28, 2005), pp. 1-4, XP 002610267, Retrieved from the Internet: URL:http://www.smartskincare.com/forum/viewtopic.php?t=410 [retrieved on Nov. 18, 2010] p. 2.
Origins Natural Resources, Cleanser Extension, Date Published Dec. 2002, www.gnpd.com, 2 pages.
Origins Natural Resources, Reflection Perfection Mattifying Face Makeup, Date Published Dec. 2000, www.gnpd.com, 2 pages.
Origins Natural Resources; Origins Home and Away; Checks and Balances to Go Set, Date Published Oct. 2009; www.gnpd.com, 4 pages.
Prescriptives Colour Cosmetics, Unmakeup Cosmetics, Date Published May 2000, www.gnpd.com, 2 pages.
Procter & Gamble Olay Anti-Wrinkle Aqua Physics, Anti-Ageing Night Cream, Date Published Mar. 2, 2010, www.gnpd.com, 3 pages.
Sagarin, *Cosmetics, Science and Technology*, 2nd Edition, vol. 1, pp. 32-43 (1972).
Sassaby Cosmetics, Jane Good Skin, Cloudburst Cleanser, Date Published Jun. 2000, www.gnpd.com, 2 pages.
SK-II Facial Clear Solution product insert, 1 page.
SK-II Facial Clear Solution, www.bloomingdale's; publicly available on or after Sep. 20, 2010, 3 pages.
Soap & Glory Cosmetics; Soap 7 Glory Skincare; The Fab Pore15-Minute Facial Peel; www.gnpd.com; Date Published Jul. 2009, 7 pages.
Stila Cosmetics, Stila Made in Your Shade; Foundation Wardrobe Light; Date Published Jul. 2009, www. gnpd.com 5 pages.
The Body Shop Seaweed; Ionic Clay Mask, Date Published Aug. 2008, www.gnpd.com, 4 pages.
The Body Shop Seaweed; Pore Protector Serum, Date Published Apr. 2008, www.gnpd.com, 2 pages.
"Treasure Chest of the Deep," Soap Perfumery and Cosmetics, vol. 64; No. 6; Jun. 1, 1991; pp. 40-41.

\* cited by examiner

REGULATION OF MAMMALIAN KERATINOUS TISSUE USING SKIN AND/OR HAIR CARE ACTIVES

CROSS REFERENCE TO RELATED APPLICATION(S)

This application claims the benefit of U.S. Provisional Application No. 61/148,081, filed Jan. 29, 2009.

FIELD OF THE INVENTION

The present invention relates to personal care compositions containing skin and/or hair care actives. Such compositions are useful for regulating the condition of mammalian keratinous tissue needing such treatments, particularly skin lightening.

BACKGROUND OF THE INVENTION

Currently, there are a number of personal care products that are available to consumers, which are directed toward improving the health and physical appearance of keratinous tissues such as the skin, hair, and nails. The majority of these products are directed to delaying, minimizing or even eliminating skin wrinkling and histological changes typically associated with the aging of skin or environmental damage to human skin. However, there also exists a need for cosmetic agents to prevent, retard, and/or treat uneven skin tone by acting as a lightening or pigmentation reduction cosmetic agent.

Mammalian keratinous tissue, particularly human skin and hair, is subjected to a variety of insults by both extrinsic and intrinsic factors. Such extrinsic factors include ultraviolet radiation, environmental pollution, wind, heat, infrared radiation, low humidity, harsh surfactants, abrasives, etc. Intrinsic factors, on the other hand, include chronological aging and other biochemical changes from within the skin. Whether extrinsic or intrinsic, these factors result in visible signs of skin damage. Typical skin damage includes thinning of the skin, which occurs naturally as one ages. With such thinning, there is a reduction in the cells and blood vessels that supply the skin as well as a flattening of the dermal-epidermal junction that results in weaker mechanical resistance of this junction. See, for example, Oikarinen, "The Aging of Skin: Chronoaging Versus Photoaging," *Photodermatol. Photoimmunol. Photomed.*, vol. 7, pp. 3-4, 1990. Other damages or changes seen in aging or damaged skin include fine lines, wrinkling, hyperpigmentation, sallowness, sagging, dark under-eye circles, puffy eyes, enlarged pores, diminished rate of turnover, and abnormal desquamation or exfoliation. Additional damage incurred as a result of both external and internal factors includes visible dead skin (i.e., flaking, scaling, dryness, roughness). For hair, these extrinsic and intrinsic factors can contribute to, among other problems, hair bleaching, split ends, fragility, roughness, hair loss, reduction in hair growth rate, and the like. Therefore, there is a need for products and methods that seek to remedy these keratinous tissue conditions.

SUMMARY OF THE INVENTION

The invention relates to a personal care composition comprising an active selected from the group consisting of phlorogine, phlorogine BG, deoxyArbutin, sucrose dilaurate, bakuchiol, pyrenoine, millet, arlatone dioic acid, cinnamic acid, ferulic acid, achromaxyl, methyl nicotinamide, oil soluble licorice extract, folic acid, undecylenic acid, zinc undecylenate, L-tryptophan, thiamine HCl, hexylresorcinol, LIPIDAMI RED VINE, dragosine, methyl gentisate, inositol, SYMDIOL 68, laminaine, their salts, their derivatives, their precursors, and/or combinations thereof; at least one additional skin and/or hair care active selected from the group consisting of sugar amines, N-acetylglucosamine, vitamin B3, retinoids, peptides, phytosterol, hexamidine, salicylic acid, N-acyl amino acid compounds, sunscreens, hesperidin, tetrahydrocurcumin, zinc pyrithione, anti-fungal agents, and yeast extract, their salts, their derivatives, their precursors, and/or combinations thereof; and a dermatologically acceptable carrier.

The invention further relates to a method for regulating the condition of mammalian keratinous tissue, the method comprising the steps of topically applying a personal care composition comprising an active selected from the group consisting of phlorogine, phlorogine BG, deoxyArbutin, sucrose dilaurate, bakuchiol, pyrenoine, millet, arlatone dioic acid, cinnamic acid, ferulic acid, achromaxyl, methyl nicotinamide, oil soluble licorice extract, folic acid, undecylenic acid, zinc undecylenate, L-tryptophan, thiamine HCl, hexylresorcinol, LIPIDAMI RED VINE, dragosine, methyl gentisate, inositol, SYMDIOL 68, laminaine, their salts, their derivatives, their precursors, and/or combinations thereof, to a desired area of tissue; and thereafter applying a second personal care composition comprising a sunscreen active to the desired area of tissue.

The invention further relates to a method for regulating the condition of mammalian keratinous tissue, the method comprising the steps of topically applying a personal care composition comprising an active selected from the group consisting of phlorogine, phlorogine BG, deoxyArbutin, sucrose dilaurate, bakuchiol, pyrenoine, millet, arlatone dioic acid, cinnamic acid, ferulic acid, achromaxyl, methyl nicotinamide, oil soluble licorice extract, folic acid, undecylenic acid, zinc undecylenate, L-tryptophan, thiamine HCl, hexylresorcinol, LIPIDAMI RED VINE, dragosine, methyl gentisate, inositol, SYMDIOL 68, laminaine, their salts, their derivatives, their precursors, and/or combinations thereof; and applying energy to the area of tissue via an energy delivery device.

DETAILED DESCRIPTION OF THE INVENTION

All percentages and ratios used herein are by weight of the total composition and all measurements made are at 25° C., unless otherwise designated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "keratinous tissue," as used herein, refers to keratin-containing layers disposed as the outermost protective covering of mammals which includes, but is not limited to, skin, hair, toenails, fingernails, cuticles, hooves, etc.

The term "topical application", as used herein, means to apply or spread the compositions of the present invention onto the surface of the keratinous tissue.

The term "dermatologically acceptable," as used herein, means that the compositions or components described are suitable for use in contact with human keratinous tissue without undue toxicity, incompatibility, instability, allergic response, and the like.

The term "safe and effective amount" as used herein means an amount of a compound or composition sufficient to significantly induce a positive benefit, preferably a positive keratinous tissue appearance or feel benefit, including independently or in combination the benefits disclosed herein, but low enough to avoid serious side effects (i.e., to provide a reasonable benefit to risk ratio, within the scope of sound judgment of the skilled artisan).

The term "post-inflammatory hyperpigmentation" as used herein refers to the changes in melanin content as a response to an inflammatory event (e.g., acne, scratch, insect sting or bite, sunburn, etc), especially in dark skin subjects.

The term "hyperpigmentation" as used herein refers to an area of skin wherein the pigmentation is greater than that of an adjacent area of skin (e.g., a pigment spot, an age spot, and the like).

The terms "desquamation, exfoliation, and/or turnover" as used herein mean the removal of the upper layers of the stratum corneum (comprising the horny layers).

The terms "oily and/or shiny appearance" as used herein mean the glossy look mammalian skin tends to exhibit upon the excretion of oil, sebum, and/or sweat from the respective source gland.

The term "sagging" as used herein means the laxity, slackness, or the like condition of skin that occurs as a result of loss of, damage to, alterations to, and/or abnormalities in dermal elastin.

The term "smoothing" and "softening" as used herein means altering the surface of the keratinous tissue such that its tactile feel is improved.

The term "sallowness" as used herein means the pale color, yellow color or the like condition of skin that occurs as a result of a loss of, damage to, alterations to, and/or abnormalities in skin components such that they become colored (e.g., yellow in color) due to processes such as protein glycation and accumulation of lipofuscin or in the decrease in peripheral blood flow that typically accompanies skin aging.

The compositions of the present invention are useful for topical application and for regulating keratinous tissue condition. Regulation of keratinous tissue condition, especially human skin condition, is often required due to conditions that may be induced or caused by factors internal and/or external to the body. For instance, "regulating skin condition" includes prophylactically regulating and/or therapeutically regulating skin condition, and may involve one or more of the following benefits: thickening (i.e., building the epidermis and/or dermis layers of the skin and/or the subcutaneous layers such as fat and muscle and where applicable the keratinous layers of the nail and hair shaft) to reduce atrophy (e.g., of the skin), increasing the convolution of the dermal-epidermal border, non-melanin skin discoloration such as under eye circles, blotching (e.g., uneven red coloration due to, e.g., rosacea) (hereinafter referred to as "red blotchiness"), sallowness (pale or yellow color), discoloration caused by telangiectasia or spider vessels, discolorations due to melanin (e.g., pigment spots, age spots, uneven pigmentation) and other chromophores in the skin (e.g., lipofuscin, protein crosslinks such as those that occur with glycation, and the like). As used herein, prophylactically regulating skin condition includes delaying, minimizing and/or preventing visible and/or tactile discontinuities in skin (e.g., texture irregularities, fine lines, wrinkles, sagging, stretch marks, cellulite, puffy eyes, and the like in the skin which may be detected visually or by feel). As used herein, therapeutically regulating skin condition includes ameliorating (e.g., diminishing, minimizing and/or effacing) discontinuities in skin. Regulating skin condition involves improving skin appearance and/or feel.

As used herein, "regulating skin condition" is intended to include regulation of such signs irrespective of the mechanism of origin.

The compositions of the present invention, including the essential and optional components thereof, are described in detail hereinafter.

I. Personal Care Composition

A. Actives

The present invention may include actives selected from the group consisting of phlorogine, phlorogine BG, deoxyArbutin, sucrose dilaurate, bakuchiol, pyrenoine, millet, arlatone dioic acid, cinnamic acid, ferulic acid, achromaxyl, methyl nicotinamide, oil soluble licorice extract, folic acid, undecylenic acid, zinc undecylenate, L-tryptophan, thiamine HCl, hexylresorcinol, LIPIDAMI RED VINE, dragosine, methyl gentisate, inositol, SYMDIOL 68, laminaine, their salts, their derivatives, their precursors, and/or combinations thereof.

The actives of the present invention may be useful in skin lightening. Skin lightening may occur through multiple mechanisms including anti-oxidant mechanisms, trypsin inhibition, anti-inflammatory mechanisms, nitric oxide scavenging, tyrosinase inhibition, etc. Thus, compounds which have these mechanisms have the potential to lighten skin.

1. Phlorogine and Phlorogine BG

The composition of the present invention may include a safe and effective amount of phlorogine (*Laminaria Saccharina* Extract). When present, the composition contains phlorogine and/or phlorogine BG in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% phlorogine and/or phlorogine BG by weight of the total composition. The phlorgine useful herein can also include derivatives and salts thereof. Phlorogine is a combination of water, PG, and *laminaria saccharina* extract. The phlorogine BG is a combination of water, BG, and *laminaria saccharina* extract. Phlorogine and phlorogine BG can be purchased from various suppliers, including Biotech Marine, France.

2. DeoxyArbutin

The composition of the present invention may include a safe and effective amount of deoxyArbutin. When present, the composition contains deoxyArbutin in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% deoxyArbutin by weight of the total composition. The deoxyArbutin useful herein can includes derivatives and salts thereof. DeoxyArbutin can be purchased from various suppliers, including Girindus, Germany.

3. Sucrose Dilaurate

The compositions of the present invention may include a safe and effective amount of sucrose dilaurate. When present, the composition contains sucrose dilaurate in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% sucrose dilaurate by weight of the total composition.

The sucrose dilaurate useful herein also includes derivatives and salts thereof.

Sucrose dilaurate can be purchased from various suppliers, including Cognis Monheim, Germany.

4. Bakuchiol

The compositions of the present invention may include a safe and effective amount of bakuchiol. Bakuchiol is known as phenol, 4-[(1E,3S)-3-ethenyl-3,7-dimethyl-1,6 octadienyl] or monterpene phenol. When present, the composition contains Bakuchiol in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% Bakuchiol by weight of the total composition The bakuchiol useful herein also includes derivatives and salts thereof. Bakuchiol can be purchased under the name SYTENOL A from various suppliers, including Sython ltd., USA.

5. Pyrenoine

The compositions of the present invention may include a safe and effective amount of pyrenoine. Pyrenoine comprises BG, water, algae extract and is rich in polyphenol. When present, the composition contains pyrenoine in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% pyrenoine by weight of the total composition.

The pyrenoine useful herein also includes derivatives and salts thereof.

Pyrenoine can be purchased from various suppliers, including Biotech Marine, France.

6. Millet

The compositions of the present invention may include a safe and effective amount of millet. When present, the composition contains millet in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% millet by weight of the total composition.

The millet useful herein includes *panicum miliaceum* seed extract. The millet useful herein also includes derivatives thereof.

Millet can be purchased from various suppliers, including Alban Muller, France.

7. Arlatone Dioic Acid (ODA White)

The compositions of the present invention may include a safe and effective amount of arlatone dioic acid. Arlatone dioic acid can comprise octadecenedioic acid. When present, the composition contains arlatone dioic acid in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% arlatone dioic acid by weight of the total composition.

Arlatone dioic acid can be purchased from various suppliers, including Sederma.

8. Cinnamic Acid

The compositions of the present invention may include a safe and effective amount of cinnamic acid. When present, the composition contains cinnamic acid in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% cinnamic acid by weight of the total composition.

Cinnamic acid can be purchased from various suppliers, including Hofmen International.

9. Ferulic Acid

The compositions of the present invention may include a safe and effective amount of ferulic acid. When present, the composition contains ferulic acid in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% Ferulic acid by weight of the total composition.

Ferulic acid can be purchased from various suppliers, including Tsuno rice fine chemicals, co. ltd., Japan.

10. Achromaxyl

The compositions of the present invention may include a safe and effective amount of achromaxyl. Achromaxyl is *brassica napus* extract. When present, the composition contains achromaxyl in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% achromaxyl by weight of the total composition.

Achromaxl can be purchased from various suppliers, including ISP and/or Vincence.

11. Methyl Nicotinamide

The compositions of the present invention may include a safe and effective amount of methyl nicotinamide. When present, the composition contains methyl nicotinamide in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% Methyl Nicotinamide by weight of the total composition.

Methyl nicotinamide can be purchased from various suppliers, including TCI America Laboratory Chemicals.

12. Oil Soluble Licorice Extract

The compositions of the present invention may include a safe and effective amount of oil soluble licorice extract. When present, the composition contains oil soluble licorice extract in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% oil soluble licorice extract by weight of the total composition.

Oil soluble licorice extract can be purchased from various suppliers, including Bioland.

13. Folic Acid

The compositions of the present invention may include a safe and effective amount of folic acid. When present, the composition contains folic acid in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% folic acid by weight of the total composition.

Folic acid can be purchased from various suppliers, including Active Concepts LLC, South Plainfield N.J.

14. Undecylenic Acid

The compositions of the present invention may include a safe and effective amount of undecylenic acid (also known as undecenoic acid). Undecylenic acid is an organic unsaturated fatty acid derived from natural castor oil. When present, the composition contains undecylenic acid in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% undecylenic acid by weight of the total composition.

Undecylenic Acid can be purchased from various suppliers, including CasChem Inc., Bayonne N.J.

15. Zinc Undecylenate

The compositions of the present invention may include a safe and effective amount of zinc undecylenate. When present, the composition contains zinc undecylenate an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% zinc undecylenate by weight of the total composition.

Zinc undecylenate can be purchased from various suppliers, including Vevy Europe SpA Genova, Italy.

16. L-tryptophan

The compositions of the present invention may include a safe and effective amount of L-tryptophan. When present, the composition contains L-tryptophan in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% L-tryptophan by weight of the total composition.

L-tryptophan can be purchased from various suppliers, including Nippon Rika, Tokyo, Japan.

17. Thiamine and Thiamine Hydrochloride

The compositions of the present invention may include a safe and effective amount of thiamine (Vitamin B1) and its hydrochloride. When present, the composition contains thiamine and its hydrochloride in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% thiamine and its hydrochloride by weight of the total composition.

Thiamine and its hydrochloride can be purchased from various suppliers, including DSM Nutritional Products Inc.

18. Hexylrescorcinol

The compositions of the present invention may include a safe and effective amount of hexylrescorcinol. When present, the composition contains hexylrescorcinol in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% hexylrescorcinol by weight of the total composition.

Hexylrescorcinol can be purchased from various suppliers, including Sytheon ltd., USA.

19. Lipidami Red Vine

The compositions of the present invention may include a safe and effective amount of LIPIDAMI RED VINE. LIPIDAMI RED VINE comprises *helianthus annuus* (sunflower) and *vitis vinifera* (grape) leaf extract. When present, the composition contains LIPIDAMI RED VINE in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% LIPIDAMI RED VINE by weight of the total composition.

LIPIDAMI RED VINE can be purchased from various suppliers, including Alban Muller, France.

20. Dragosine

The compositions of the present invention may include a safe and effective amount of dragosine. Dragosine may also be known as carnosine. When present, the composition contains dragosine in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% dragosine by weight of the total composition.

Dragosine can be purchased from various suppliers, including Symrise.

21. Methyl Gentisate

The compositions of the present invention may include a safe and effective amount of methyl gentisate. Methyl gentisate can comprise methyl 2,5-dihydroxybenzoate. When present, the composition contains methyl gentisate in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% methyl gentisate by weight of the total composition.

Methyl gentisate can be purchased from various suppliers, including Vama Famacosmetica.

22. Laminaine

The compositions of the present invention may include a safe and effective amount of laminaine. When present, the composition contains laminaine in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% laminaine by weight of the total composition.

23. SYMDIOL

The compositions of the present invention may include a safe and effective amount of SYMDIOL 68. It is a combination of 1,2-hexandiol and 1,2-octandiol. When present, the composition contains SYMDIOL 68 in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% SYMDIOL 68 by weight of the total composition. SYMDIOL 68 can be purchased from various suppliers, including Symrise.

24. Inositol

The compositions of the present invention may include a safe and effective amount of inositol. When present, the composition contains inositol in an amount from about 0.0001% to about 50%, in one embodiment from about 0.001% to about 20%, in another embodiment from about 0.01% to about 10%, by weight of the composition. In yet another embodiment the composition comprises from about 0.1% to about 5%, and in yet another embodiment from about 0.5% to about 3% inositol by weight of the total composition. Inositol can be purchased from various suppliers, including Tsuno rice fine chemicals, co. ltd., Japan.

B. Additional Skin and/or Hair Care Actives

Compositions of the present invention typically comprise a safe and effective amount of at least one additional skin and/or hair care active. A representative, non-limiting list of such actives includes sugar amines, N-acetylglucosamine, vitamin B3, retinoids, peptides, phytosterol, hexamidine, salicylic acid, N-acyl amino acid compounds, sunscreens, hesperidin, tetrahydrocurcumin, zinc pyrithione, anti-fungal agents, and yeast extract (e.g., Pitera®), their salts, their derivatives, their precursors, and/or combinations thereof. Further description of some of these additional actives is provided below.

When present, the compositions of the present invention preferably contain from about 0.0001% to about 50%, more preferably from about 0.001% to about 20%, even more preferably from about 0.01% to about 10%, by weight of the composition, of the additional skin and/or hair actives. The amounts listed herein is only to be used as a guide, as the optimum amount of the additional skin and/or hair actives used in a composition will depend on the specific active selected since their potency does vary considerably. Hence, the amount of some skin and/or hair actives useful in the present invention may be outside the ranges listed herein.

The skin and/or hair care actives of the present invention may be useful in skin lightening. Skin lightening may occur through multiple mechanisms including anti-oxidant mechanisms, trypsin inhibition, anti-inflammatory mechanisms, nitric oxide scavenging, tyrosinase inhibition, etc. Thus, compounds which have these mechanisms have the potential to lighten skin. Some of the additional skin and/or hair care actives that are useful herein are described in more detail below.

1. Sugar Amines (Amino Sugars)

The compositions of the present invention optionally include a safe and effective amount of a sugar amine, which are also known as amino sugars. The sugar amine compounds useful in the present invention are described in PCT Publication WO 02/076423 and U.S. Pat. No. 6,159,485.

As used herein, "sugar amine" includes isomers and tautomers of such and its salts (e.g., HCl salt) and is commercially available from Sigma Chemical Co. Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). In one embodiment, for use herein are glucosamine, particularly D-glucosamine and N-acetyl glucosamine, particularly N-acetyl-D-glucosamine.

2. Vitamin $B_3$

The compositions of the present invention may include a safe and effective amount of a vitamin $B_3$ compound. Vitamin $B_3$ compounds are particularly useful for regulating skin condition as described in U.S. Pat. No. 5,939,082.

As used herein, "vitamin $B_3$ compound" means a compound having the formula:

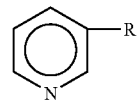

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid (e.g., tocopheryl nicotinate, myristyl nicotinate). Examples of suitable vitamin $B_3$ compounds are well known in the art and are commercially available from a number of sources (e.g., the Sigma Chemical Company, ICN Biomedicals, Inc., and Aldrich Chemical Company). A vitamin $B_3$ compound useful in the present invention is niacinamide.

3. Retinoid

The compositions of this invention may contain a safe and effective amount of a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably selected from retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), or mixtures thereof. More preferably the retinoid is a retinoid other than retinoic acid.

4. Peptide

The compositions of the present invention may contain a safe and effective amount of a peptide, including but not limited to, di-, tri-, tetra-, penta-, and hexa-peptides and derivatives thereof. In one embodiment, peptides for use herein are the dipeptide carnosine (beta-ala-his), the tripeptide gly-his-lys, the pentapeptide lys-thr-thr-lys-ser, lipophilic derivatives of peptides, and metal complexes of the above, e.g., copper complex of the tripeptide his-gly-gly (also known as lamin). In one embodiment the dipeptide derivative is palmitoyl-lys-thr. A commercially available tripeptide derivative-containing composition is Biopeptide CL®, which contains 100 ppm of palmitoyl-gly-his-lys and is commercially available from Sederma. A commercially available pentapeptide derivative-containing composition is Matrixyl®, which contains 100 ppm of palmitoyl-lys-thr-thr-lys-ser and is commercially available from Sederma.

5. Phytosterol

The topical compositions of the present invention may comprise a safe and effective amount of one or more phytosterols selected from the group consisting of β-sitosterol, campesterol, brassicasterol, Δ5-avennasterol, lupenol, α-spinasterol, stigmasterol, their derivatives, analogs, and combinations thereof. As used herein, "phytosterol" includes isomers and tautomers of such and is commercially available from Aldrich Chemical Company, Sigma Chemical Company, and Cognis.

6. Hexamidine

The topical compositions of the present invention optionally include a safe and effective amount of one or more of hexamidine compounds, its salts, and its derivatives. As used herein, hexamidine derivatives include any isomers and tautomers of hexamidine compounds including but not limited to organic acids and mineral acids, for example sulfonic acid, carboxylic acid etc. Preferably, the hexamidine compounds include hexamidine diisethionate, commercially available as Eleastab® HP100 from Laboratoires Serobiologiques.

7. N-acyl Amino Acid Compound

The topical compositions of the present invention may comprise a safe and effective amount of one or more N-acyl amino acid compounds. The amino acid can be one of any of the amino acids known in the art. Preferably, the N-acyl amino acid compound is selected from the group consisting of N-acyl Phenylalanine, N-acyl Tyrosine, their isomers, their salts, and derivatives thereof. The amino acid can be the D or L isomer or a mixture thereof. A N-acyl Amino Acid is N-undecylenoyl-L-phenylalanine. N-undecylenoyl-L-phenylalanine is commercially available under the tradename Sepiwhite® from SEPPIC.

8. Sunscreen Actives

The compositions of the subject invention may optionally contain a sunscreen active. As used herein, "sunscreen active" includes both sunscreen agents and physical sunblocks. Suitable sunscreen actives may be organic or inorganic. A wide variety of conventional sunscreen actives are suitable for use herein. Sagarin, et al., at Chapter VIII, pages 189 et seq., of *Cosmetics Science and Technology* (1972), discloses numerous suitable actives 9. Hesperedin The compositions of the present invention may include a safe and effective amount of hesperedin. Hesperedin is a flavonoid. One hesperedin is glucosyl hesperedin.

10. Tetrahydrocurcumin

The compositions of the present invention may include a safe and effective amount of tetrahydrocurcumin, its esters (e.g., diacetate ester), or combinations of these.

C. Dermatologically Acceptable Carrier

The topical compositions of the present invention also comprise a dermatologically acceptable carrier for the active materials. The phrase "dermatologically acceptable carrier", as used herein, means that the carrier is suitable for topical application to the keratinous tissue, has good aesthetic properties, is compatible with the actives of the present invention and any other components, and will not cause any safety or toxicity concerns. A safe and effective amount of carrier is from about 50% to about 99.99%, preferably from about 60% to about 99.9%, more preferably from about 70% to about 98%, and even more preferably from about 80% to about 95% of the composition.

The carrier can be in a wide variety of forms. For example, emulsion carriers, including, but not limited to, oil-in-water, water-in-oil, silicone-in-water, water-in-silicone, water-in-oil-in-water, and oil-in-water-in-silicone emulsions, are useful herein.

In one embodiment carriers comprise an emulsion such as oil-in-water emulsions and water-in-oil emulsions, e.g., silicone-in-water or water-in-silicone emulsions. As will be understood by the skilled artisan, a given component will distribute primarily into either the water or oil phase, depending on the water solubility/dispensability of the component in the composition. In one embodiment oil-in-water emulsions are especially preferred.

Emulsions according to the present invention generally contain a solution as described above and a lipid or oil. Lipids and oils may be derived from animals, plants, or petroleum and may be natural or synthetic (i.e., man-made). In one embodiment emulsions also contain a humectant, such as glycerin. Emulsions will preferably further contain from about 0.1% to about 10%, more preferably from about 0.2% to about 5%, of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986).

Suitable emulsions may have a wide range of viscosities, depending on the desired product form. Exemplary low viscosity emulsions, can have a viscosity of about 50 centistokes or less in one embodiment, in another embodiment about 10 centistokes or less, and in yet another embodiment about 5 centistokes or less.

The use of dipropylene glycol monocaprylate would be a suitable solvent for use with oil soluble actives. When present, the composition contains the dipropylene glycol monocaprylate in an amount of from about 0.1% to about 20%, preferably from about 1% to about 10%, and more preferably from about 5% to about 7%, by weight of the total composition. An example of dipropylene glycol monocaprylate is Caproyl 90, which can be purchased from Gattefosse, Gennevilliers, France.

The use of isopropyl lauroyl sarcosinate would also be a suitable solvent for use with oil soluble actives. When present, the composition contains the isopropyl lauroyl sarcosinate in an amount of from about 0.1% to about 20%, preferably from about 1% to about 10%, and more preferably from about 5% to about 7%, by weight of the total composition. An example of isopropyl lauroyl sarcosinate is Eldew, which can be purchased from Ajinomoto U.S.A., Paramus, N.J.

Some actives suitable for use with dipropylene glycol monocaprylate or isopropyl lauroyl sarcosinate include, but are not limited to, tetrahydrocurcumin, tetrahydrocurmin diacetate, glycyrrhizic acid, glycyrrhetinic acid, lauryl p-cresol ketoxime, bis-abolol and ginger extract, alpha-linoleic acid, oil soluble vitamin C, carnosic acid and ursolic acid, proanthocyanidins, green tea polyphenols, oleuropein, xymenynic acid, ethyl p-methoxycinnamate, and lupeol hemisuccinate. Either dipropylene glycol monocaprylate or isopropyl lauroyl sarcosinate can be used to solublize these compounds alone or in combination with additional compounds, either oil or water soluble, or combinations thereof. The structures of dipropylene glycol monocaprylate and isopropyl lauroyl sarcosinate are shown below:

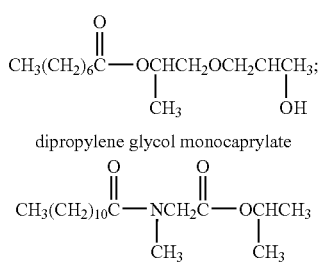

dipropylene glycol monocaprylate isopropyl lauroyl sarcosinate.

The compositions of the present invention can also comprise other dermatologically acceptable topical carriers and can also comprise oral carriers. For example, another topical carrier can be a surfactant-containing cleanser (e.g., bar, shampoo, foaming cleanser, liquid cleanser, body wash, cleansing cloth, and the like). In such a carrier, the surfactant can be anionic, cationic, zwitterionic, nonionic, or mixtures of these. Another topical carrier example is a color cosmetic (lipstick, rouge, eye liner, mascara, foundation, nail polish, and the like). An oral carrier can be a beverage, food item, pill, capsule, powder, caplet, and the like.

D. Optional Components

The compositions of the present invention may contain a variety of other ingredients that are conventionally used in given product types provided that they do not unacceptably alter the benefits of the invention.

The optional components, when incorporated into the composition, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, anti-caking agents, antifoaming agents, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, and thickeners.

The compositions of the present invention may also include the synthetic cationic polymer Polyquaternium-37 (methacryloylethyl trimethyl ammonium chloride homopolymer). This polymer may be added to the compositions as a powder or as a liquid dispersion. This polymer is commercially available under the tradenames Synthalen (3V Sigma), Ultragel 300 (Cosmetic Rheologies Ltd.), Rheocare CTH(E) (Cosmetic Rheologies Ltd.), Salcare SC95 and Salcare SC96 (Ciba Specialty Chemicals).

Other optional components useful in the present invention include those described in U.S. Publication No. 2004/0175347A1, including desquamation actives, such as salicylic acid and zwitterionic surfactants; soothing and/or healing agents; skin treating agents; skin sensates, astringents, etc. (e.g., clove oil, menthol, camphor, eucalyptus oil, eugenol, menthyl lactate, witch hazel distillate); anti-acne actives, such as resorcinol, sulfur, erythromycin, zinc, dehydroacetic acid; anti-wrinkle actives/anti-atrophy actives; anti-oxidants/radical scavengers, such as tocopherol; chelators, such as furildioxime and derivatives thereof; flavonoids; anti-inflammatory agents; anti-cellulite agents; tanning actives such as dihydroxyacetone; skin lightening agents; antimicrobial and antifungal actives; sunscreen actives; conditioning agents such as glycerol, urea, petrolatum, sucrose polyester, and combinations thereof; thickening agents such as carboxylic acid polymers, crosslinked polyacrylate polymers, polyacrylamide polymers, polysaccharides, gums; water-soluble vitamins; and particulate materials. Compositions of the present invention may contain a safe and effective amount of one or more of the following other actives or ingredients: fatty acids (especially poly-unsaturated fatty acids), glucosamine, zinc pyrithione (ZPT), thiol compounds (e.g., N-acetyl cysteine, glutathione, thioglycolate), other vitamins (e.g., B1, B2, B5, B6, B12, C, D, E, F, K, P), beta-carotene, ubiquinone, idebenone, amino acids, minerals (e.g., Zn, Mn, Mg, Cu, Fe, and Se), hydroxy acids (e.g., alpha-hydroxy acids, alpha-keto acids, and beta-hydroxy acids), kojic aid, arbutin, mulberry extract, exfoliation agents, anti-dandruff agents, and the like.

II. Composition Forms

The topical compositions of the subject invention, including but not limited to lotions, milks, mousses, serums, sprays, aerosols, foams, sticks, pencils, gels, creams and ointments, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. Sagarin, *Cosmetics, Science and Technology*, 2nd Edition, Vol. 1, pp. 32-43 (1972), contains numerous examples of materials suitable as an emollient. In one embodiment the emollient is glycerin. Glycerin is used in an amount of from about 0.001% to about 20% in one embodiment, in another embodiment from about 0.01% to about 15%, and in yet another embodiment from about 0.1% to about 10% by weight of the composition.

Compositions of this invention useful for cleansing ("cleansers") are formulated with a suitable carrier (e.g., as described above, and from about 1% to about 90%, by weight of the composition, of a dermatologically acceptable surfactant).

The physical form of the cleansing compositions is not critical. The compositions can be, for example, formulated as toilet bars, liquids, shampoos, bath gels, hair conditioners, hair tonics, pastes, or mousses. Toilet bars are preferred since this is the form of cleansing agent most commonly used to wash the skin. Rinse-off cleansing compositions, such as shampoos, require a delivery system adequate to deposit sufficient levels of actives on the skin and scalp. In one embodiment the delivery system involves the use of insoluble complexes. For a more complete disclosure of such delivery systems, see U.S. Pat. No. 4,835,148.

The compositions of the present invention may also be in the form of cosmetics. Suitable cosmetic forms include, but are not limited to, foundations, lipsticks, rouges, mascaras, and the like. Such cosmetic products may include conventional ingredients such as oils, colorants, pigments, emollients, fragrances, waxes, stabilizers, and the like. Exemplary carriers and such other ingredients which are suitable for use herein are described, for example, in U.S. Pat. No. 6,060,547.

The compositions of the present invention may also be in the form of shave prep products, including, for example, gels, foams, lotions, and creams; and include both aerosol and non-aerosol versions.

III. Composition Preparation

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

IV. Methods for Regulating Keratinous Tissue Condition

The compositions of the present invention are useful for regulating a number of mammalian keratinous tissue conditions. Such regulation of keratinous tissue conditions includes prophylactic and therapeutic regulation. More specifically, such regulating methods are directed to, but are not limited to, thickening keratinous tissue (i.e., building the epidermis and/or dermis and/or subcutaneous layers of the skin and where applicable the keratinous layers of the nail and hair shaft), preventing, retarding, improving, and/or treating uneven skin tone by acting as a lightening or pigmentation reduction cosmetic agent, preventing, retarding, and/or treating atrophy of mammalian skin, softening and/or smoothing lips, hair and nails of a mammal, preventing, retarding, and/or treating itch of mammalian skin, preventing, retarding, and/or treating the appearance of dark under-eye circles and/or puffy eyes, preventing, retarding, and/or treating sallowness of mammalian skin, preventing, retarding, and/or treating sagging (i.e., glycation) of mammalian skin, preventing and/or retarding tanning of mammalian skin, desquamating, exfoliating, and/or increasing turnover in mammalian skin, reducing the size of pores in mammalian skin, regulating oily/shiny appearance of mammalian skin, preventing, retarding, and/or treating hyperpigmentation such as post-inflammatory hyperpigmentation, preventing, retarding, and/or treating the appearance of spider vessels and/or red blotchiness on mammalian skin, preventing, retarding, and/or treating fine lines and wrinkles of mammalian skin, preventing, retarding, and/or treating skin dryness (i.e., roughness, scaling, flaking) and preventing, retarding, and/or treating the appearance of cellulite in mammalian skin. The compositions of the present invention may also be useful in inhibiting hair growth, reducing shaving frequency, improving ease of shaving, decreasing shaving frequency, making hair softer and/or finer, making hair less noticeable, slowing the re-growth of hair, reducing erythema and/or irritation to skin, making skin smoother and/or silkier, and improving the hair removal process. Regulating keratinous tissue condition involves topically applying to the keratinous tissue a safe and effective amount of a composition of the present invention. The amount of the composition that is applied, the frequency of application and the period of use will vary widely depending upon the level of skin and/or hair care actives and/or other components of a given composition and the level of regulation desired.

In one embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), in one embodiment it is preferred that chronic applications continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions, which are typically applied per application, are in mg composition/$cm^2$ skin, from about 0.1 mg/$cm^2$ to about 20 mg/$cm^2$. A particularly useful application amount is about 0.5 mg/$cm^2$ to about 10 mg/$cm^2$.

Treating keratinous tissue condition can be practiced, for example, by applying a composition in the form of a skin lotion, clear lotion, milky lotion, cream, gel, foam, ointment, paste, emulsion, spray, aerosol, conditioner, tonic, cosmetic, lipstick, foundation, nail polish, after-shave, roll-on or deodorant stick, powder, oil or the like which is intended to be left on the skin or other keratinous tissue for some aesthetic, prophylactic, therapeutic or other benefit (i.e., a "leave-on" composition). After applying the composition to the keratinous tissue (e.g., skin), it is preferably left on for a period of at least about 15 minutes, more preferably at least about 30 minutes, even more preferably at least about 1 hour, even more preferably for at least several hours, e.g., up to about 12 hours. Any part of the external portion of the face, hair, and/or nails can be treated, (e.g., face, lips, under-eye area, eyelids, scalp, neck, torso, arms, hands, legs, feet, fingernails, toenails, scalp hair, eyelashes, eyebrows, etc.) The composition can be dispensed from a bottle, jar, tube, sachet, pouch, container, tottle, vial, ampule, compact, etc. or can be integrally contained within a delivery form such as a wipe. The application of the present compositions may be done using the palms of the hands and/or fingers. The application may also be done with the aid of a device or implement such as a cotton ball, swab, pad, brush, eye dropper, puff, sponge, wand, wipe, foam, nonwoven substrate, mask, roll-on applicator, stick applicator, applicator pen, spray applicator, atomizer, razor, etc. The active may be contained in a rupturable pouch between two substrates.

In another embodiment, the application of the topical composition is subsequent to a skin treatment such as cleansing, exfoliation or tanning.

Another approach to ensure a continuous exposure of the keratinous tissue to at least a minimum level of the composition is to apply the compound by use of a patch applied, e.g., to the face. Such an approach is particularly useful for problem skin areas needing more intensive treatment (e.g., facial crows feet area, frown lines, under eye area, upper lip, and the like). The patch can be occlusive, semi-occlusive or non-occlusive, and can be adhesive or non-adhesive. The composition can be contained within the patch or be applied to the skin prior to application of the patch. The patch can also include additional actives such as chemical initiators for exothermic reactions such as those described in PCT application WO 9701313, and in U.S. Pat. Nos. 5,821,250, 5,981,547, and 5,972,957 to Wu, et al. The patch can also contain a source of electrical energy (e.g., a battery) to, for example, increase delivery of the composition and active agents (e.g., iontophoresis). The patch is preferably left on the keratinous tissue for a period of at least about 5 minutes, more preferably at least about 15 minutes, more preferably still at least about 30 minutes, even more preferably at least about 1 hour, even more preferably at night as a form of night therapy.

Another approach to enhancing the benefits of the actives is use of a kit or regimen of 2 or 3 or 4 or more products and/or treatment procedures (e.g., exfoliation followed by topical treatment with one or more of the actives of the present invention, depilation of hair followed by topical treatment with one or more of the actives of the present invention, and the like). The various components of a regimen can be used in a short period of time (e.g., within an hour) or spread over a longer time frame within a day (e.g., morning and evening) or over even longer time periods (e.g., one step in the regimen done weekly or monthly and the other steps in the regimen done on a more regular basis, e.g., daily).

Combinations of an oral composition and a topical composition can be packaged together as a kit. In another embodiment, the oral composition and the topical composition are not packaged together as a kit, but potential users of the regimen are informed (e.g., through advertisements, product labeling) that the oral and the topical compositions may be used in conjunction with one another to regulate the condition of keratinous tissue.

The present invention also contemplates the delivery of energy, via a device, to keratinous tissue, either simultaneously and/or sequentially (e.g., within 10 minutes) with application of the topical compositions. The energy delivery device may deliver energy in a variety of forms, including but not limited to energy in the form of light, heat, sound (including ultrasonic waves), magnetic energy, electromagnetic energy (including radiofrequency waves and microwaves), mechanical energy (exfoliating or microdermabrasion device), and combinations thereof. The delivery of energy may be continuous, pulsed, modulated, non-modulated, and combinations thereof. In one embodiment, the energy delivery device is hand-held. Alternatively, the energy delivery device is cordless.

The energy may be applied by holding a device within a single area of keratinous tissue, and subsequently moving the device to another area of tissue (or "stamping"). Alternatively, the energy may be applied as the device is continuously moved, or scanned, across the surface of the tissue. The device may be held in substantially continuous contact with the surface of the keratinous tissue, as with laser devices, or may be held at a short distance from the keratinous tissue with the energy directed toward the surface, as with flash lamps.

A temperature change may be simultaneously induced in the keratinous tissue or alternatively, in a compound applied to the surface of the tissue. This temperature change is in addition to any temperature change induced by the delivered energy itself. For example, the keratinous tissue may be slightly warmed prior to delivery of energy, or alternatively, the keratinous tissue may be cooled after delivery of energy.

For energy derived from ultraviolet light sources, the wavelength will generally fall within the UV-A range, from about 315 to about 400 nm (nanometer). For energy derived from visible light sources, the wavelength will generally range from about 400 nm to about 700 nm. For energy derived from infrared (IR) light sources, the wavelength will generally range from about 700 nm to about to about 3000 nm. The amount of energy delivered, or "output fluence," may be in the range of about 1 $J/cm^2$ to about 100 $J/cm^2$, where "J" means Joules. For pulsed light sources, the pulse length may range from about 0.001 seconds to about 3 seconds, with an average pulse duration of from about 0.001 seconds to about 1 second. The surface area of keratinous tissue to be covered will vary depending on the application. These and other parameters relevant to delivery of energy depend upon the type of treatment and the type of tissue to be treated, and will appropriately be selected by one of skill in the art.

The present invention also provides articles of commerce that include the personal care compositions described herein, wherein at least one of the personal care composition, packaging for the personal care composition, and advertisement material pertaining to the personal care composition comprises indicia and/or an image which communicates to a consumer that the personal care composition can be used in conjunction with an energy delivery device for regulating the condition of mammalian keratinous tissue.

The present invention also provides methods of marketing personal care compositions for preventing, retarding, and/or treating uneven skin tone. One method of marketing such compositions includes making available to a consumer a personal care composition described herein and communicating to the consumer that the topical application of the personal care composition may improve the consumer's skin color. The manner in which the communication is conveyed to the consumer is non-limiting. By way of example only, the communication can be effected by known advertisement techniques, such as, television, internet and magazine advertisements. The communication may be a point-of-sale technique, such as, for example, a shelf and/or floor affixed communication. And the communication may take the form of indicia (text, symbols, colors, shades, figures, and the like) disposed in and/or on packaging of the personal care compositions.

Methods of conducting business are also contemplated by the present invention. One method includes the step of communicating to a consumer a comparison between a first personal care composition comprising an active discussed herein and a second personal care composition that does not include the noted active. The comparison may relate to skin tone, skin lightening, skin whitening, pigmentation, among other parameters associated with regulating mammalian keratinous tissue conditions.

EXAMPLES

The following are non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

| Component | A | B | C | D | E | F |
|---|---|---|---|---|---|---|
| Disodium EDTA | 0.100 | 0.100 | 0.100 | 0.100 | 0.100 | 0.100 |
| phlorogine | 2.000 | 0 | 0 | 0 | 0 | 0 |
| Phlorogine BG | 0 | 2.000 | 0 | 0 | 0 | 0 |
| deoxyArbutin | 0 | 0 | 2.000 | 0 | 0 | 0 |
| sucrose dilaurate | 0 | 0 | 0 | 2.000 | 0 | 0 |
| Bakuchiol | 0 | 0 | 0 | 0 | 2.000 | 0 |
| pyrenoine | 0 | 0 | 0 | 0 | 0 | 2.000 |
| Niacinamide | 5.000 | 5.000 | 5.000 | 5.000 | 5.000 | 5.000 |
| Isohexadecane | 3.000 | 3.000 | 3.000 | 3.000 | 3.000 | 3.000 |
| Isopropyl isostearate | 1.330 | 1.330 | 1.330 | 1.330 | 1.330 | 1.330 |
| Sucrose polycottonseedate | 0.670 | 0.670 | 0.670 | 0.670 | 0.670 | 0.670 |
| Polymethylsilsesquioxane | 0.250 | 0.250 | 0.250 | 0.250 | 0.250 | 0.250 |
| Cetearyl glucoside + cetearyl alcohol | 0.200 | 0.200 | 0.200 | 0.200 | 0.200 | 0.200 |
| Behenyl alcohol | 0.400 | 0.400 | 0.400 | 0.400 | 0.400 | 0.400 |
| Ethylparaben | 0.200 | 0.200 | 0.200 | 0.200 | 0.200 | 0.200 |
| Propylparaben | 0.100 | 0.100 | 0.100 | 0.100 | 0.100 | 0.100 |
| Cetyl alcohol | 0.320 | 0.320 | 0.320 | 0.320 | 0.320 | 0.320 |
| Stearyl alcohol | 0.480 | 0.480 | 0.480 | 0.480 | 0.480 | 0.480 |
| Tocopheryl acetate | 0.500 | 0.500 | 0.500 | 0.500 | 0.500 | 0.500 |
| PEG-100 stearate | 0.100 | 0.100 | 0.100 | 0.100 | 0.100 | 0.100 |
| Glycerin | 7.000 | 7.000 | 7.000 | 7.000 | 7.000 | 7.000 |
| Titanium dioxide | 0.604 | 0.604 | 0.604 | 0.604 | 0.604 | 0.604 |
| Polyacrylamide + C13-14 isoparaffin + laureth-7 | 2.000 | 2.000 | 2.000 | 2.000 | 2.000 | 2.000 |
| Panthenol | 1.000 | 1.000 | 1.000 | 1.000 | 1.000 | 1.000 |
| Benzyl alcohol | 0.400 | 0.400 | 0.400 | 0.400 | 0.400 | 0.400 |
| Dimethicone + dimethiconol | 2.000 | 2.000 | 2.000 | 2.000 | 2.000 | 2.000 |
| Water (to 100 g) | to 100 | to 100 | to 100 | to 100 | to 100 | to 100 |
| TOTAL | 100 | 100 | 100 | 100 | 100 | 100 |

| Component | G | H | I | J | K | L |
|---|---|---|---|---|---|---|
| Disodium EDTA | 0.100 | 0.100 | 0.100 | 0.100 | 0.100 | 0.100 |
| millet | 2.000 | 0 | 0 | 0 | 0 | 0 |
| arlatone dioic acid | 0 | 2.000 | 0 | 0 | 0 | 0 |
| cinnamic acid | 0 | 0 | 2.000 | 0 | 0 | 0 |
| achromaxyl | 0 | 0 | 0 | 2.000 | 0 | 0 |
| methyl nicotinamide | 0 | 0 | 0 | 0 | 2.000 | 0 |
| oil soluble licorice extract | 0 | 0 | 0 | 0 | 0 | 2.000 |
| Niacinamide | 5.000 | 5.000 | 5.000 | 5.000 | 5.000 | 5.000 |
| Isohexadecane | 3.000 | 3.000 | 3.000 | 3.000 | 3.000 | 3.000 |
| Isopropyl isostearate | 1.330 | 1.330 | 1.330 | 1.330 | 1.330 | 1.330 |
| Sucrose polycottonseedate | 0.670 | 0.670 | 0.670 | 0.670 | 0.670 | 0.670 |
| Polymethylsilsesquioxane | 0.250 | 0.250 | 0.250 | 0.250 | 0.250 | 0.250 |
| Cetearyl glucoside + cetearyl alcohol | 0.200 | 0.200 | 0.200 | 0.200 | 0.200 | 0.200 |
| Behenyl alcohol | 0.400 | 0.400 | 0.400 | 0.400 | 0.400 | 0.400 |
| Ethylparaben | 0.200 | 0.200 | 0.200 | 0.200 | 0.200 | 0.200 |
| Propylparaben | 0.100 | 0.100 | 0.100 | 0.100 | 0.100 | 0.100 |
| Cetyl alcohol | 0.320 | 0.320 | 0.320 | 0.320 | 0.320 | 0.320 |
| Stearyl alcohol | 0.480 | 0.480 | 0.480 | 0.480 | 0.480 | 0.480 |
| Tocopheryl acetate | 0.500 | 0.500 | 0.500 | 0.500 | 0.500 | 0.500 |
| PEG-100 stearate | 0.100 | 0.100 | 0.100 | 0.100 | 0.100 | 0.100 |
| Glycerin | 7.000 | 7.000 | 7.000 | 7.000 | 7.000 | 7.000 |
| Titanium dioxide | 0.604 | 0.604 | 0.604 | 0.604 | 0.604 | 0.604 |
| Polyacrylamide + C13-14 isoparaffin + laureth-7 | 2.000 | 2.000 | 2.000 | 2.000 | 2.000 | 2.000 |
| Panthenol | 1.000 | 1.000 | 1.000 | 1.000 | 1.000 | 1.000 |
| Benzyl alcohol | 0.400 | 0.400 | 0.400 | 0.400 | 0.400 | 0.400 |
| Dimethicone + dimethiconol | 2.000 | 2.000 | 2.000 | 2.000 | 2.000 | 2.000 |
| Water (to 100 g) | to 100 | to 100 | to 100 | to 100 | to 100 | to 100 |
| TOTAL | 100 | 100 | 100 | 100 | 100 | 100 |

| Component | M | N | O | P | Q |
|---|---|---|---|---|---|
| Disodium EDTA | 0.100 | 0.100 | 0.100 | 0.100 | 0.100 |
| folic acid | 2.000 | 0 | 0 | 0 | 0 |
| undecylenic acid | 0 | 2.000 | 0 | 0 | 0 |
| zinc undecylenate | 0 | 0 | 2.000 | 0 | 0 |
| L-tryptophan | 0 | 0 | 0 | 2.000 | 0 |
| thiamine HCl | 0 | 0 | 0 | 0 | 2.000 |
| Niacinamide | 5.000 | 5.000 | 5.000 | 5.000 | 5.000 |
| Isohexadecane | 3.000 | 3.000 | 3.000 | 3.000 | 3.000 |

-continued

| | | | | | |
|---|---|---|---|---|---|
| Isopropyl isostearate | 1.330 | 1.330 | 1.330 | 1.330 | 1.330 |
| Sucrose polycottonseedate | 0.670 | 0.670 | 0.670 | 0.670 | 0.670 |
| Polymethylsilsesquioxane | 0.250 | 0.250 | 0.250 | 0.250 | 0.250 |
| Cetearyl glucoside + cetearyl alcohol | 0.200 | 0.200 | 0.200 | 0.200 | 0.200 |
| Behenyl alcohol | 0.400 | 0.400 | 0.400 | 0.400 | 0.400 |
| Ethyl paraben | 0.200 | 0.200 | 0.200 | 0.200 | 0.200 |
| Propylparaben | 0.100 | 0.100 | 0.100 | 0.100 | 0.100 |
| Cetyl alcohol | 0.320 | 0.320 | 0.320 | 0.320 | 0.320 |
| Stearyl alcohol | 0.480 | 0.480 | 0.480 | 0.480 | 0.480 |
| Tocopheryl acetate | 0.500 | 0.500 | 0.500 | 0.500 | 0.500 |
| PEG-100 stearate | 0.100 | 0.100 | 0.100 | 0.100 | 0.100 |
| Glycerin | 7.000 | 7.000 | 7.000 | 7.000 | 7.000 |
| Titanium dioxide | 0.604 | 0.604 | 0.604 | 0.604 | 0.604 |
| Polyacrylamide + C13-14 isoparaffin + laureth-7 | 2.000 | 2.000 | 2.000 | 2.000 | 2.000 |
| Panthenol | 1.000 | 1.000 | 1.000 | 1.000 | 1.000 |
| Benzyl alcohol | 0.400 | 0.400 | 0.400 | 0.400 | 0.400 |
| Dimethicone + dimethiconol | 2.000 | 2.000 | 2.000 | 2.000 | 2.000 |
| Water (to 100 g) | to 100 | to 100 | to 100 | to 100 | to 100 |
| TOTAL | 100 | 100 | 100 | 100 | 100 |

| Component | R | S | T | U | V |
|---|---|---|---|---|---|
| Disodium EDTA | 0.100 | 0.100 | 0.100 | 0.100 | 0.100 |
| hexylresorcinol | 2.000 | 0 | 0 | 0 | 0 |
| LIPIDAMI RED VINE | 0 | 2.000 | 0 | 0 | 0 |
| dragosine | 0 | 0 | 2.000 | 0 | 0 |
| methyl gentisate | 0 | 0 | 0 | 2.000 | 0 |
| Ferulic acid | 0 | 0 | 0 | 0 | 2.000 |
| Niacinamide | 5.000 | 5.000 | 5.000 | 5.000 | 5.000 |
| Isohexadecane | 3.000 | 3.000 | 3.000 | 3.000 | 3.000 |
| Isopropyl isostearate | 1.330 | 1.330 | 1.330 | 1.330 | 1.330 |
| Sucrose polycottonseedate | 0.670 | 0.670 | 0.670 | 0.670 | 0.670 |
| Polymethylsilsesquioxane | 0.250 | 0.250 | 0.250 | 0.250 | 0.250 |
| Cetearyl glucoside + cetearyl alcohol | 0.200 | 0.200 | 0.200 | 0.200 | 0.200 |
| Behenyl alcohol | 0.400 | 0.400 | 0.400 | 0.400 | 0.400 |
| Ethylparaben | 0.200 | 0.200 | 0.200 | 0.200 | 0.200 |
| Propylparaben | 0.100 | 0.100 | 0.100 | 0.100 | 0.100 |
| Cetyl alcohol | 0.320 | 0.320 | 0.320 | 0.320 | 0.320 |
| Stearyl alcohol | 0.480 | 0.480 | 0.480 | 0.480 | 0.480 |
| Tocopheryl acetate | 0.500 | 0.500 | 0.500 | 0.500 | 0.500 |
| PEG-100 stearate | 0.100 | 0.100 | 0.100 | 0.100 | 0.100 |
| Glycerin | 7.000 | 7.000 | 7.000 | 7.000 | 7.000 |
| Titanium dioxide | 0.604 | 0.604 | 0.604 | 0.604 | 0.604 |
| Polyacrylamide + C13-14 isoparaffin + laureth-7 | 2.000 | 2.000 | 2.000 | 2.000 | 2.000 |
| Panthenol | 1.000 | 1.000 | 1.000 | 1.000 | 1.000 |
| Benzyl alcohol | 0.400 | 0.400 | 0.400 | 0.400 | 0.400 |
| Dimethicone + dimethiconol | 2.000 | 2.000 | 2.000 | 2.000 | 2.000 |
| Water (to 100 g) | to 100 | to 100 | to 100 | to 100 | to 100 |
| TOTAL | 100 | 100 | 100 | 100 | 100 |

| Component | W | X | Y |
|---|---|---|---|
| Disodium EDTA | 0.100 | 0.100 | 0.100 |
| SYMDIOL | 2.000 | 0 | 0 |
| laminaine | 0 | 2.000 | 0 |
| Inositol | 0 | 0 | 2.000 |
| Niacinamide | 5.000 | 5.000 | 5.000 |
| Isohexadecane | 3.000 | 3.000 | 3.000 |
| Isopropyl isostearate | 1.330 | 1.330 | 1.330 |
| Sucrose polycottonseedate | 0.670 | 0.670 | 0.670 |
| Polymethylsilsesquioxane | 0.250 | 0.250 | 0.250 |
| Cetearyl glucoside + cetearyl alcohol | 0.200 | 0.200 | 0.200 |
| Behenyl alcohol | 0.400 | 0.400 | 0.400 |
| Ethylparaben | 0.200 | 0.200 | 0.200 |
| Propylparaben | 0.100 | 0.100 | 0.100 |
| Cetyl alcohol | 0.320 | 0.320 | 0.320 |
| Stearyl alcohol | 0.480 | 0.480 | 0.480 |
| Tocopheryl acetate | 0.500 | 0.500 | 0.500 |
| PEG-100 stearate | 0.100 | 0.100 | 0.100 |
| Glycerin | 7.000 | 7.000 | 7.000 |

-continued

| | | | |
|---|---|---|---|
| Titanium dioxide | 0.604 | 0.604 | 0.604 |
| Polyacrylamide + C13-14 isoparaffin + laureth-7 | 2.000 | 2.000 | 2.000 |
| Panthenol | 1.000 | 1.000 | 1.000 |
| Benzyl alcohol | 0.400 | 0.400 | 0.400 |
| Dimethicone + dimethiconol | 2.000 | 2.000 | 2.000 |
| Water (to 100 g) | to 100 | to 100 | to 100 |
| TOTAL | 100 | 100 | 100 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a) an active selected from the group consisting of sucrose dilaurate, a salt thereof, a combination of 1,2-hexanediol and 1,2-octanediol, and combinations thereof;
   b) from about 0.01% to about 10%, by weight of the composition, of at least one additional skin and/or hair care active selected from the group consisting of niacinamide, nicotinic acid, nicotinyl alcohol, a salt of any of the foregoing, a nicotinic acid ester, and combinations thereof; and
   c) a dermatologically acceptable carrier;
   wherein when the composition comprises sucrose dilaurate or a salt thereof, it comprises from about 0.1% to about 5%, by weight of the composition, of said sucrose dilaurate or a salt thereof, and when the composition comprises a combination of 1,2-hexanediol and 1,2-octanediol, it comprises from about 0.1% to about 5%, by weight of the composition, of said combination.

2. The personal care composition of claim 1, wherein said carrier comprises a solvent selected from the group consisting of dipropylene glycol monocaprylate and isopropyl lauroyl sarcosinate.

3. The personal care composition of claim 1 wherein the composition comprises from about 0.5% to about 3%, by weight of the composition, of sucrose dilaurate or salt thereof.

4. A personal care composition comprising:
   a) from about 0.1% to about 5%, by weight of the composition, of an active selected from the group consisting of sucrose dilaurate, a salt thereof, and combinations thereof;
   b) from about 0.01% to about 10%, by weight of the composition, of at least one additional skin and/or hair care active selected from the group consisting of niacinamide, nicotinic acid, nicotinyl alcohol, a salt of any of the foregoing, a nicotinic acid ester, and combinations thereof; and
   c) a dermatologically acceptable carrier.

5. The personal care composition of claim 1 wherein the composition comprises from about 0.5% to about 3%, by weight of the composition, of a combination of 1,2-hexanediol and 1,2-octanediol.

6. A method for regulating the condition of mammalian keratinous tissue, the method comprising the steps of:
   (a) topically applying the personal care composition of claim 1; and
   (b) thereafter applying a second personal care composition comprising a sunscreen active to the desired area of tissue.

7. The method of claim 6, further comprising the step of:
   (c) applying energy to the area of tissue via an energy delivery device.

8. The method of claim 7, wherein step (c) is performed simultaneously, at least in part, and/or sequentially with performance of step (a).

9. The method of claim 7, wherein the energy is applied in a form selected from the group consisting of light, heat, sound, magnetic energy, electromagnetic energy, mechanical, and combinations thereof.

10. The method of claim 6, wherein step (b) is performed within 10 minutes of performing step (a).

11. The personal care composition of claim 4 wherein the composition comprises from about 0.01% to about 10%, by weight of the composition, of niacinamide.

12. The personal care composition of claim 4, wherein said carrier comprises a solvent selected from the group consisting of dipropylene glycol monocaprylate and isopropyl lauroyl sarcosinate.

13. The personal care composition of claim 4 further comprising from about 0.5% to about 5%, by weight of the composition, of a combination of 1,2-hexanediol and 1,2-octanediol.

14. The personal care composition of claim 4 wherein the composition comprises from about 0.5% to about 3%, by weight of the composition, of sucrose dilaurate, salt thereof or combination thereof.

15. The personal care composition of claim 14 wherein the composition comprises from about 0.01% to about 10%, by weight of the composition, of niacinamide.

16. The personal care composition of claim 15 wherein the weight ratio of (i) the niacinamide to (ii) the sucrose dilaurate, salt thereof, or combination thereof is from about 2.5:1 to about 5:1.

17. A personal care composition comprising:
a) from about 0.1% to about 5%, by weight of the composition, of a combination of 1,2-hexanediol and 1,2-octanediol;
b) from about 0.01% to about 10%, by weight of the composition, of at least one additional skin and/or hair care active selected from the group consisting of niacinamide, nicotinic acid, nicotinyl alcohol, a salt of any of the foregoing, a nicotinic acid ester, and combinations thereof; and
c) a dermatologically acceptable carrier.

18. The personal care composition of claim 17 wherein the composition comprises from about 0.5% to about 3%, by weight of the composition, of the combination of 1,2-hexanediol and 1,2-octanediol.

19. The personal care composition of claim 18 wherein the composition comprises from about 0.01% to about 10%, by weight of the composition, of niacinamide.

20. The personal care composition of claim 19 wherein the weight ratio of (i) the niacinamide to (ii) 1,2-hexanediol and 1,2-octanediol is from about 2.5:1 to about 5:1.

* * * * *